United States Patent
Ferrari et al.

(10) Patent No.: US 11,192,969 B2
(45) Date of Patent: Dec. 7, 2021

(54) METHOD FOR ISOMER REDUCTION DURING POLYMERIZATION AND SYSTEM FOR ACCOMPLISHING THE SAME

(71) Applicant: DOW GLOBAL TECHNOLOGIES LLC, Midland, MI (US)

(72) Inventors: Daniela Ferrari, Rosharon, TX (US); Sean Ewart, Pearland, TX (US); Timothy Gambrel, Lake Jackson, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 130 days.

(21) Appl. No.: 16/062,934

(22) PCT Filed: Dec. 14, 2016

(86) PCT No.: PCT/US2016/066735
§ 371 (c)(1),
(2) Date: Jun. 15, 2018

(87) PCT Pub. No.: WO2017/106392
PCT Pub. Date: Jun. 22, 2017

(65) Prior Publication Data
US 2019/0023823 A1    Jan. 24, 2019

Related U.S. Application Data

(60) Provisional application No. 62/268,074, filed on Dec. 16, 2015.

(51) Int. Cl.
*C08F 210/16* (2006.01)
*C08F 2/01* (2006.01)
(Continued)

(52) U.S. Cl.
CPC ........... *C08F 210/16* (2013.01); *C07C 7/20* (2013.01); *C08F 2/01* (2013.01); *C08F 2/38* (2013.01);
(Continued)

(58) Field of Classification Search
CPC .. C08F 210/16; C08F 2/38; C08F 2/40; C08F 2/42; C08F 2/01
(Continued)

(56) References Cited

U.S. PATENT DOCUMENTS

| 3,139,460 A | 6/1964 | Eisenmann |
| 4,634,744 A * | 1/1987 | Hwang ................. C08F 10/02 526/84 |

(Continued)

FOREIGN PATENT DOCUMENTS

| EP | 0193263 A1 | 9/1986 | |
| WO | WO 2009/155155 A1 * | 12/2009 | ............... C08K 5/00 |

(Continued)

OTHER PUBLICATIONS

International Search Report for International Application No. PCT/US2016/066735, International filing date Dec. 14, 2016, dated Mar. 16, 2017, 6 pages.

(Continued)

*Primary Examiner* — Rip A Lee
(74) *Attorney, Agent, or Firm* — Cantor Colburn LLP

(57) ABSTRACT

Disclosed herein is a method for reducing isomerization during the copolymerization of ethylene with an α-olefin comprising adding to a reactor a reaction mixture comprising hydrogen, ethylene, an α-olefin, a solvent and a catalyst; where the catalyst does not include a chain shuttling agent that comprises dialkyl zinc; heating the reactor to a first temperature to react the ethylene with the α-olefin to form a copolymer; discharging from the reactor a first product (Continued)

stream to a heat exchanger; where the product stream comprises the copolymer; adding to the product stream prior to the heat exchanger a first additive that is operative to reduce isomerization of the α-olefin; and discharging from the heat exchanger a second product stream.

21 Claims, 1 Drawing Sheet

(51) Int. Cl.
| | |
|---|---|
| *C08F 2/38* | (2006.01) |
| *C08F 4/80* | (2006.01) |
| *C07C 7/20* | (2006.01) |
| *C08J 11/02* | (2006.01) |
| *C08K 5/092* | (2006.01) |
| *C08K 5/098* | (2006.01) |
| *C08K 5/11* | (2006.01) |
| *C08K 5/134* | (2006.01) |
| *C08K 5/17* | (2006.01) |
| *C08L 27/14* | (2006.01) |
| *C08L 27/16* | (2006.01) |
| *C08L 27/18* | (2006.01) |
| *C08L 27/20* | (2006.01) |

(52) U.S. Cl.
CPC ............... *C08F 4/80* (2013.01); *C08J 11/02* (2013.01); *C08K 5/092* (2013.01); *C08K 5/098* (2013.01); *C08K 5/11* (2013.01); *C08K 5/134* (2013.01); *C08K 5/17* (2013.01); *C08L 27/14* (2013.01); *C08L 27/16* (2013.01); *C08L 27/18* (2013.01); *C08L 27/20* (2013.01); *C08F 2410/01* (2013.01); *Y02P 20/582* (2015.11)

(58) Field of Classification Search
USPC .............................................. 526/82, 83, 84
See application file for complete search history.

(56) References Cited

U.S. PATENT DOCUMENTS

| | | | |
|---|---|---|---|
| 4,701,504 A | 10/1987 | Mitchell et al. | |
| 4,777,229 A | 10/1988 | Zboril et al. | |
| 5,118,757 A * | 6/1992 | McCullough, Jr. ... | C08F 210/00 525/53 |
| 6,828,395 B1 * | 12/2004 | Ehrman ................. | C08F 10/00 525/191 |
| 7,906,614 B2 * | 3/2011 | Vanspeybroeck ....... | C08F 10/02 528/482 |
| 7,999,046 B2 * | 8/2011 | Vanspeybroeck ......... | C08F 6/02 526/82 |
| 8,933,156 B2 * | 1/2015 | Castelluccio ........... | C08L 53/00 524/394 |
| 9,221,936 B2 * | 12/2015 | Kuo ....................... | C08F 10/02 |
| 9,290,594 B2 * | 3/2016 | Camp ................... | C08F 210/16 |
| 9,428,636 B2 * | 8/2016 | Effler ..................... | C08K 5/524 |
| 9,988,475 B2 * | 6/2018 | Chen ..................... | C08F 210/16 |
| 10,336,846 B2 * | 7/2019 | Ewart ................... | C08F 210/18 |
| 2008/0281037 A1 | 11/2008 | Karjala et al. | |
| 2011/0207903 A1 | 8/2011 | Fontaine et al. | |
| 2014/0178614 A1 | 6/2014 | Demirors et al. | |
| 2016/0108186 A1 * | 4/2016 | Wang .................. | C08F 4/65904 525/240 |
| 2017/0101354 A1 * | 4/2017 | Brown ................... | C08F 10/02 |
| 2017/0305811 A1 * | 10/2017 | Shin ....................... | B01J 31/188 |

FOREIGN PATENT DOCUMENTS

| | | | | |
|---|---|---|---|---|
| WO | WO-2013052308 A1 * | 4/2013 | ........... | C08F 210/16 |
| WO | 2014138854 A1 | 9/2014 | | |
| WO | 2016191076 A1 | 12/2016 | | |

OTHER PUBLICATIONS

Written Opinion for international Application No. PCT/US2016/066735, International filing date Dec. 14, 2016, dated Mar. 16, 2017, 11 pages.

* cited by examiner

METHOD FOR ISOMER REDUCTION DURING POLYMERIZATION AND SYSTEM FOR ACCOMPLISHING THE SAME

CROSS REFERENCE TO RELATED APPLICATIONS

This application is a National Stage application of PCT/US2016/066735, filed Dec. 14, 2016, which claims the benefit of U.S. Provisional Application No. 62/268,074, filed Dec. 16, 2015, both of which are incorporated by reference in their entirety herein.

BACKGROUND

This disclosure relates to a method for $\alpha$-olefin isomerization reduction during polymerization and to a system for accomplishing the same. In particular, this disclosure relates to a method for isomerization reduction during the production of polyolefins.

Alpha olefins (such as, for example, 1-octene, 1-hexene, 1-butene, and the like) are copolymerized with ethylene to manufacture a polyethylene copolymer. FIG. 1 is a depiction of an exemplary process 10 that is presently used for producing a polyethylene copolymer that contains ethylene and octene. The process 10 utilizes a reactor 12 into which reactants such as hydrogen, ethylene, octene, catalyst and solvent are added. During the reaction a portion of the octene added to the reactor is polymerized with the ethylene to form the copolymer which is then discharged along with any unreacted monomers and comonomers in a product stream to a heat exchanger 14 and a devolatilizer 16. Only the 1-octene isomer (instead of other isomeric forms) participates in the polymerization reaction.

A heat exchanger (HE) 14 disposed downstream of the reactor increases the temperature of the product stream before entering the devolatilizer 16. However, during the heating step, the isomerization of octene results in the formation of 2-octene, 3-octene and 4-octene isomers that are inert to the polymerization process. Water is added to the product stream upstream of the heat exchanger 14 and an anti-oxidant is added to the product stream downstream of the heat exchanger 14. A devolatilizer 16 disposed downstream of the heat exchanger 14 removes any unreacted ethylene, solvent or octene and recycles it to the reactor 12 to undergo further polymerization. The isomerization of octene to 2-octene, 3-octene and 4-octene isomers is undesirable because it reduces the yield of the copolymer.

It is therefore desirable to retain the octene in its 1-octene isomeric form during the production of the polyethylene copolymer.

SUMMARY

Disclosed herein is a method for reducing isomerization during the copolymerization of ethylene with an $\alpha$-olefin comprising adding to a reactor a reaction mixture comprising hydrogen, ethylene, an $\alpha$-olefin, a solvent and a catalyst; where the catalyst does not include a chain shuttling agent that comprises dialkyl zinc; heating the reactor to a first temperature to react the ethylene with the $\alpha$-olefin to form a copolymer; discharging from the reactor a first product stream to a heat exchanger; where the product stream comprises the copolymer; adding to the product stream prior to the heat exchanger a first additive that is operative to reduce isomerization of the $\alpha$-olefin; and discharging from the heat exchanger a second product stream.

Disclosed herein too is a method for reducing isomerization during the copolymerization of ethylene with 1-octene comprising adding to a reactor a reaction mixture comprising hydrogen, ethylene, an $\alpha$-olefin, a solvent, a first additive and a catalyst; where the catalyst does not include a chain shuttling agent that comprises dialkyl zinc; and where the first additive is operative to reduce isomerization of the $\alpha$-olefin; heating the reactor to a first temperature to react the ethylene with the $\alpha$-olefin to form a copolymer; discharging from the reactor a first product stream to a heat exchanger; where the product stream comprises the copolymer; and discharging from the heat exchanger a second product stream.

Disclosed herein too is a system comprising a reactor that is operative to react a reaction mixture comprising hydrogen, ethylene, a solvent, an $\alpha$-olefin, and a catalyst to form a polyethylene copolymer; where the catalyst does not include a chain shuttling agent that comprises dialkyl zinc; and a heat exchanger that is operative to receive a product stream containing the polyethylene copolymer from the reactor in addition to receiving an additive that is operative to reduce isomerization of the $\alpha$-olefin.

Disclosed herein too is a system comprising a reactor that is operative to react a reaction mixture comprising hydrogen, ethylene, a solvent, an $\alpha$-olefin, an additive and a catalyst to form a polyethylene copolymer; where the catalyst does not include a chain shuttling agent that comprises dialkyl zinc; and where the additive is operative to reduce isomerization of the $\alpha$-olefin; and a heat exchanger that is operative to receive a product stream containing the polyethylene copolymer from the reactor.

DETAILED DESCRIPTION

Disclosed herein is a method for reducing the amount of isomerization of $\alpha$-olefins that occur during the polymerization with ethylene to produce and ethylene copolymer. More specifically, disclosed herein is a method for reducing the amount of octene that is converted into 2-octene, 3-octene and 4-octene obtained during the production of a polyethylene copolymer. The method comprises adding an additive upstream of the reactor and/or upstream of the heat exchanger that reduces octene isomerization and hydrogenation. In a preferred embodiment, the additive is added upstream of only the heat exchanger and downstream of the reactor to reduce the isomerization of the $\alpha$-olefin during the manufacturing of the ethylene copolymer.

Figure 1:
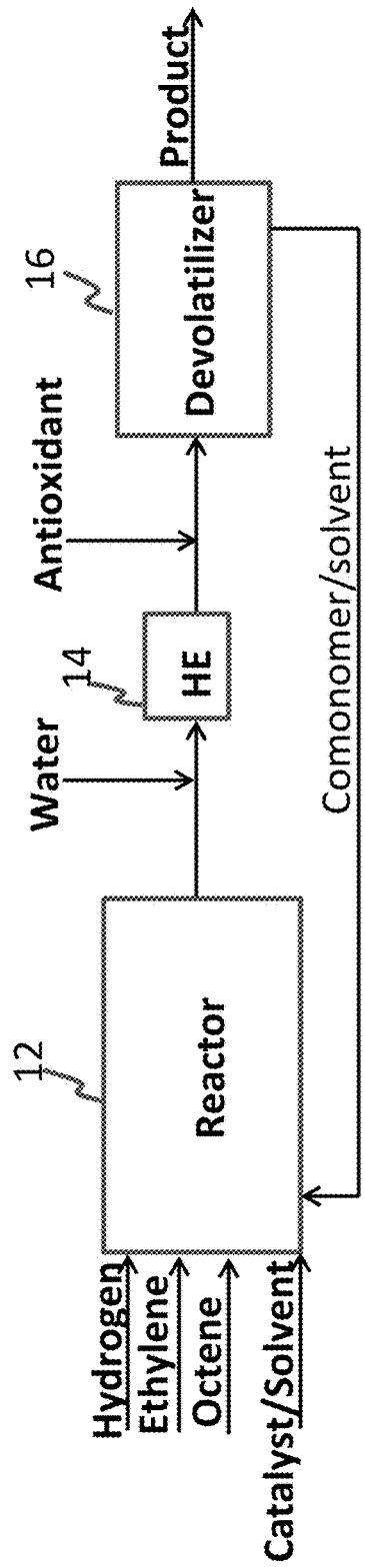
FIG. 1 is a depiction of an exemplary prior art process that is used for producing a polyethylene copolymer that contains ethylene and octene.
Figure 2:
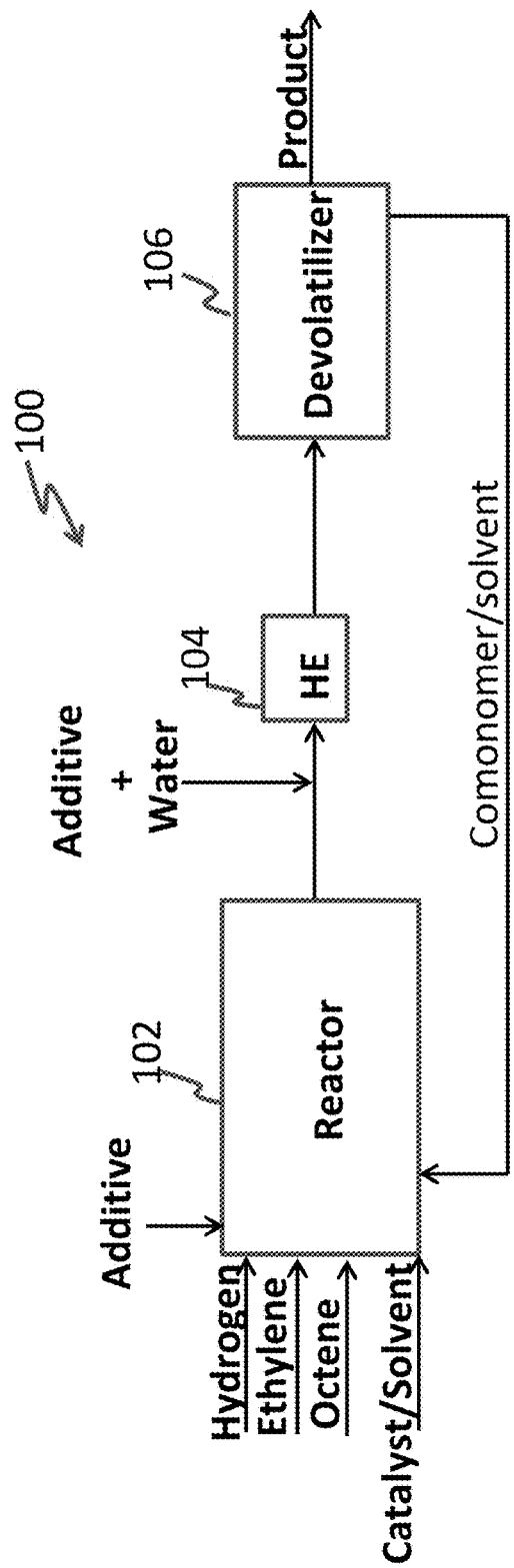
FIG. 2 is a depiction of an exemplary process that reduces the isomerization of 1-octene during the production of the polyethylene copolymer that contains ethylene and octene.

FIG. 2 is a depiction of an exemplary embodiment of a process 100 for reducing the amount of undesirable $\alpha$-olefin isomers. The system 100 comprises a reactor 102 that is operative to receive reactants that produce a polyethylene copolymer. The reactants are hydrogen, ethylene, an $\alpha$-olefin, a catalyst and a solvent. The catalyst is a molecular catalyst that does not include a chain shuttling agent that comprises zinc. In an embodiment, the catalyst is a molecular catalyst that does not include a chain shuttling agent that comprises dialkyl zinc.

A first additive that is operative to minimize isomerization of the α-olefin is also added to the reactor 102. The system 100 further comprises a heat exchanger (HE) 104 and a devolatilizer 106 both of which lie downstream of the reactor 102 and are in fluid communication with the reactor 102. The heat exchanger 104 is generally operated at a higher temperature than the reactor 102. The devolatilizer 106 lies downstream of the heat exchanger 104 and is in fluid communication with it. The heat exchanger 104 receives a first product stream that comprises a copolymer of ethylene and α-olefin along with unreacted reactants and other byproducts from the reactor 102.

Water and a second additive are added downstream of the reactor 102 and upstream of the heat exchanger 104. The second additive is operative to reduce isomerization of the α-olefin during the heating in the heat exchanger 104. The devolatilizer 106 receives a second product stream from the heat exchanger. The term "second product stream" is used to distinguish the "first product stream" from the "second product stream" and is not meant to indicate that the devolatilizer 106 receives two product streams from the heat exchanger 104. As noted above, the temperature of the product stream leaving the heat exchanger 104 is greater than the temperature of the product stream entering the heat exchanger 104.

In an embodiment, the first additive may be the same as the second additive or different from it. Both the first additive and the second additive reduce isomerization of the α-olefin during the polymerization process.

In an embodiment, a third additive may be added downstream of the heat exchanger 104. The third additive may be the same or different from the first additive and the second additive. In an embodiment, the first additive, the second additive and the third additive are the same additive and function to reduce isomerization of the α-olefin during the polymerization process.

The α-olefins that undergo isomerization in the absence of the additive are 1-butene, 1-hexene, 1-octene, 1-decene, 1-dodecene, 1-tetradecene, 1-hexadecene, 1-octadecene, or the like, or a combination thereof. In an embodiment, a preferred α-olefin is 1-octene.

It is desirable for the additives that are added to the reactor 102 and the heat exchanger 104 to comprise moieties that reduce isomerization of the α-olefins during the polymerization process. Examples of such moieties are hydroxyls, amines, carboxylic acids, esters of carboxylic acids, phosphates, fluorine, or a combination thereof. Preferred additives that may be added to the reactor and/or to the product stream prior to or after the heat exchanger are aromatic species having one or more hydroxyl functionalities, amines (e.g., primary amines, secondary amines, tertiary amines, cyclic amines, hindered amines, and the like), fluoropolymers, fatty acids (e.g., stearic acids), salts of fatty acids (e.g., stearates), esters of fatty acids, or the like, or a combination thereof. It is desirable for the additives to avoid catalyst deactivation and participating in the polymerization of the ethylene with the α-olefins and thus becoming part of the copolymer.

Aromatic species having one or more hydroxyl functionalities may be used as the additive. Aromatic species having the following structure shown in the formula (1) can be used:

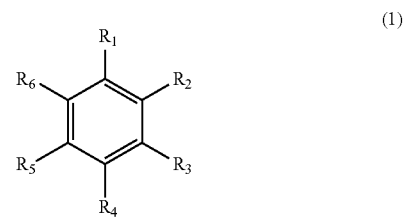

where one or more of $R_1$ through $R_6$ is a hydroxyl group, with the remainder of $R_1$ through $R_6$ being independently a hydrogen, a substituted or unsubstituted $C_1$-$C_{15}$ alkyl group, a substituted or unsubstituted $C_1$-$C_{15}$ cycloalkyl group, a substituted or unsubstituted $C_1$-$C_{15}$ ester group, or a halogen group.

Examples or the aromatic species of the formula (1) that may be used as the additive are phenol, dihydroxybenzene (e.g., catechol, resorcinol and hydroquinone), trihydroxybenzene (e.g., hydroxyquinol, phloroglucinol, and pyrogallol), tetrahydroxybenzene (e.g., benzenetetrol), alkylphenol (e.g., cresols, xylenols, propylphenol, butylphenol, amylphenol, heptylphenol, octylphenol, nonylphenol, dodecylphenol and related "long chain alkylphenols" (LCAPs)), or the like, or a combination thereof.

Bisphenol-type dihydroxy aromatic compounds may also be used as the additive and may include some of the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, 1,2-bis(4-hydroxyphenyl)ethane, 2-(4-hydroxyphenyl)-2-(3-hydroxyphenyl)propane, bis(4-hydroxyphenyl) phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantine, (alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, or the like, or a combination comprising at least one of the foregoing dihydroxy aromatic compounds.

Exemplary phenols are Irganox 1010 commercially available from BASF and IRGANOX 1076 commercially available from Ciba.

Primary amines have one of three hydrogen atoms in ammonia is replaced by an alkyl or aromatic. Examples of primary amines include methylamine, ethanolamine, octylamine, aniline, or the like, or a combination thereof.

Secondary amines have two organic substituents (alkyl, aryl or both) bound to the nitrogen atom of ammonia together with one hydrogen (or no hydrogen if one of the substituent bonds is a double bond). Examples of secondary amines include dimethylamine and methylethanolamine, diphenylamine or the like, or a combination thereof.

In tertiary amines, all three hydrogen atoms are replaced by organic substituents. Examples include trimethylamine, triphenylamine, trioctylamine, or the like, or a combination thereof.

Cyclic amines are either secondary or tertiary amines. Examples of cyclic amines include the 3-member ring aziridine and the six-membered ring piperidine. N-methylpiperidine and N-phenylpiperidine are examples of cyclic tertiary amines.

Some of the aromatic secondary and tertiary amines listed above are termed hindered amines. Examples of hindered amines are n,n'-bis(1,4-dimethylpentyl-p-phenylenediamine), alkylated diphenylamines, 4,4'-bis(alpha, alpha-dimethylbenzyl)diphenylamine, diphenyl-p-phenylenediamine, mixed di-aryl-p-phenylenediamines, 1,8-bis(dimethylamino)naphthalene, N',N',N',N'-tetramethyl-1,8-naphthalenediamiine, or the like, or a combination thereof. Examples of hindered amines are CHIMASSORB 2020, CHIMASSORB 119, CHIMASSORB 994, and CGL 116 commercially available from BASF Plastic Additives.

Additives that comprise carboxylic acid functional groups are useful for reducing the isomerization. Fatty acids are a useful group of additives for use in the reactor and/or in the heat exchanger. A fatty acid is a carboxylic acid with a long aliphatic tail (chain), which is either saturated or unsaturated. Most naturally occurring fatty acids have a chain of an even number of carbon atoms, from 12 to 28. Examples of saturated fatty acids are caprylic acid, capric acid, lauric acid, myristic acid, palmitic acid, stearic acid, arachidic acid, behenic acid, lignoceric acid, cerotic acid, or the like, or a combination thereof. Examples of unsaturated fatty acids are myristoleic acid, palmitoleic acid, sapienic acid, oleic acid, elaidic acid, vaccenic acid, linoleic acid, linoelaidic acid, arachidonic acid, eicosapentaenoic acid, erucic acid, docosahexaenoic acid, or the like, or a combination thereof. Without being limited to theory, the carboxylic acid groups present in the fatty acids can reduce isomerization of the α-olefin in the heat exchanger. A preferred fatty acid for use in minimizing isomerization of α-olefins is stearic acid.

Salts and esters of fatty acids may also be used as additives. Fatty acid salts of Group I and II metals are useful for reducing isomerization of the α-olefins. Preferred salts of fatty acids are lithium (Li), sodium (Na), potassium (K), rubidium (Rb), caesium (Cs), magnesium (Mg), calcium (Ca), strontium (Sr), and barium (Ba) salts, or a combination thereof.

Potassium, sodium, calcium and magnesium salts of the fatty acids are more preferred. In an embodiment, potassium, sodium, calcium and magnesium salts of stearic acid are preferred. Sodium stearate, potassium stearate, magnesium stearate, calcium stearate or a combination thereof are especially preferred as additives for minimizing the isomerization of α-olefins. Preferred esters of fatty esters are fatty acid alkyl esters. Fatty acid methyl esters and fatty acid ethyl esters are preferred.

Fluoropolymers may also be used as additives for minimizing the isomerization of α-olefins. Examples of fluoropolymers are polyvinyl fluoride, polyvinylidene fluoride, polytetrafluoroethylene, polychlorotrifluoroethylene, polyhexafluoropropylene, polyperfluoropropylvinylether, polyperfluoromethylvinylether, or the like, or a combination thereof. The fluoropolymers may be homopolymers, block copolymers, random copolymers, star block copolymers, alternating copolymers, or combinations thereof. Combinations of the foregoing fluoropolymers can include blends of the fluoropolymers that are not reactively bonded to each other.

The fluoropolymers have weight average molecular weights (Mw) of 500 to 10,000, preferably 1,000 to 8,000 and more preferably 1,500 to 5,000 grams per mole (g/mole). An exemplary commercially available fluoropolymer is DYNAMAR 5920A commercially available from 3M Advanced Materials.

Phosphates may also be used as an additive to reduce isomerization. Phosphates are salts of phosphoric acid $H_3PO_4$.

Phosphate salts having the structure of formula (2) may be used

(2)

where one or more of $R_1$, $R_2$ or $R_3$ is hydrogen, and where the remainder of $R_1$, $R_2$ or $R_3$ are either metal ions, or organic groups that comprise a substituted or unsubstituted $C_1$-$C_{15}$ alkyl group, or a substituted or unsubstituted $C_1$-$C_{15}$ cycloalkyl group. The salts can therefore be organic or inorganic salts. Inorganic salts generally have the structure of formula (3) below:

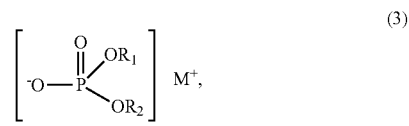

(3)

where M is sodium, calcium, potassium, rubidium, cesium, ammonium, or the like, and where one or more of $R_1$ and $R_2$ are hydrogen atoms.

In an embodiment, in the formula (2), two of the R groups (i.e., any two of $R_1$, $R_2$ or $R_3$) and may be joined together to provide a cyclic group, for example, diphenyl pentaerythritol diphosphate. Other suitable phosphates can be aromatic phosphates, such as, for example, phenyl bis(dodecyl)phosphate, phenyl bis(neopentyl)phosphate, phenyl bis(3,5,5'-trimethylhexyl)phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, tri(nonylphenyl)phosphate, bis(dodecyl)p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like.

Polymeric phosphates can also be used as additives. Di- or polyfunctional aromatic phosphorus-containing compounds are also useful, for example, compounds of the formulas below:

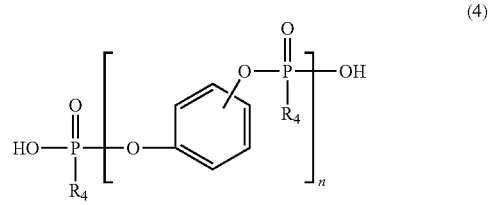

(4)

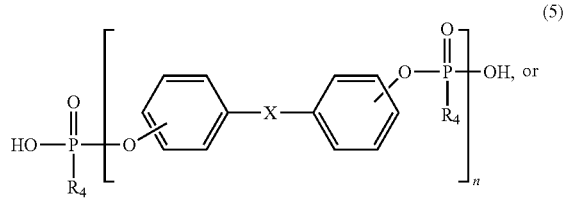

(5)

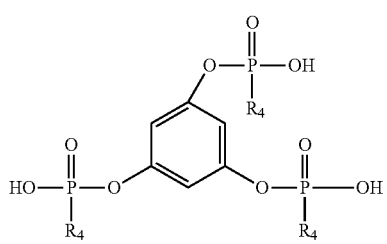

(6)

wherein each $R_4$ is a hydroxyl, a hydrocarbon having 1 to 15 carbon atoms; a hydrocarbonoxy having 1 to 15 carbon atoms and n is 1 to 30. Examples of suitable di- or polyfunctional aromatic phosphorus-containing compounds include the bis(diphenyl) phosphate of hydroquinone and the bis(diphenyl)phosphate of bisphenol-A (and respectively, their oligomeric and polymeric counterparts, or the like, or a combination thereof.

The additives can be added in amounts of up to 5,000 parts per million (ppm), preferably 1 to 3,000 ppm and more preferably 10 to 2,000 ppm based on a total weight of the copolymer manufactured.

In an embodiment, in order to manufacture a copolymer of ethylene and α-olefin at a high yield, reactants such as hydrogen, ethylene, α-olefin, a catalyst, and a solvent are added to the reactor. The reactor is generally operated at a temperature of 160 to 210° C. An optional additive such as, for example, one of those listed above may be added to the first reactor along with the reactants.

Upon conversion of a portion of the ethylene and α-olefin to the copolymer in the reactor, unreacted reactants along with the desired product (the copolymer of ethylene and octene) and other byproducts are charged to the heat exchanger to be heated further. The heat exchanger is generally operated at a higher temperature than the reactor in order to facilitate devolatilization of solvent and other small molecules in the devolatilizer. The heat exchanger is generally operated at a temperature of 215 to 270° C. To the product stream emanating from the reactor is added the additive along with water. A product stream from the heat exchanger is charged to the devolatilizer. Additional additive may optionally be added to the product stream being charged to the devolatilizer. The copolymer product along with any undesirable byproducts are removed from the devolatilizer while unreacted reactants are recycled back to the reactor to undergo further processing.

By adding the additive to the product stream at a point between the reactor and the heat exchanger instead of downstream of the heat exchanger, the amount of α-olefin isomerization is reduced by 10 to 100 percent, preferably by 30 to 70 weight percent as compared with a process where the additive is added downstream of the heat exchanger, all other factors remaining unchanged.

The isomerization decrease (wt %) is defined as:

$$\frac{\left(\begin{array}{c}1-\text{octene isomerized in baseline} - \\ 1-\text{octene isomerized in current run}\end{array}\right)}{1-\text{octene isomerized in baseline}} * 100$$

The hydrogenation decrease (wt %) is defined as:

$$\frac{\left(\begin{array}{c}1-\text{octene hydrogenated in baseline} - \\ 1-\text{octene hydrogenated in current run}\end{array}\right)}{1-\text{octene hydrogenated in baseline}} * 100$$

The reduction of octene loss (wt %) is defined as:

$$\frac{\left(\begin{array}{c}\text{total } 1-\text{octene loss in baseline} - \\ \text{total } 1-\text{octene loss in current run}\end{array}\right)}{\text{total } 1-\text{octene loss in baseline}} * 100$$

The process and the system detailed herein are exemplified by the following non-limiting example.

EXAMPLES

Example 1

This example was conducted to demonstrate the advantages of adding the additive upstream of the heat exchanger instead of downstream of the heat exchanger. In a pilot plant, a mixture of 1-octene, Isopar-E (solvent) was fed to the reactor and subsequent heat exchanger without addition of catalyst or co-catalyst to create a baseline (see run 1 in Table 1 below). Hydrogen was then added to measure the increased octene isomerization and hydrogenation based on mass balance and gas chromatography (GC) analysis (see run 2 in Table 1). The same conditions as for run 2 were used to produce a baseline before the addition of each additive (see runs 4, 10, 12, 14, and 16 in Table 1 respectively). The additives were mixed with Isopar-E and added at a total flow rate of 2 pounds per hour. Shown in parenthesis is the actual flow rate for each additive in grams per hour (g/h). In the additive tank, water is also present to give a water flow rate of 0.26 g/h for all runs.

For all additives and combinations of additives tested, the octene losses due to hydrogenation and isomerization were reduced from 14 to 49 weight percent compared to the baseline experiments. The results are shown in the Table 1 below.

TABLE 1

| Run | Octene lb/h | Isopar E lb/h | H2 sccm | Additive (g/h) | water g/h | Reactor Temp. °C. | Heat Exchanger Temp. °C. | octene isomerized % | octene hydrogenated % | total octene loss total % | isomerization decrease % | hydrogenation decrease % | reduction octene loss % |
|---|---|---|---|---|---|---|---|---|---|---|---|---|---|
| 1 | 10.5 | 24.4 | — | — | — | 180 | 240 | 0.15 | 0.00 | 0.15 | | | |
| 4 | 10.5 | 24.5 | 300 | — | — | 180 | 240 | 1.01 | 0.53 | 1.54 | | | |
| 7 | 10.5 | 26.4 | 300 | Stearic Acid (5.45) | 0.26 | 180 | 240 | 0.60 | 0.39 | 0.99 | 40.7 | 26.9 | 36.0 |
| 10 | 10.5 | 24.4 | 300 | — | — | 180 | 240 | 1.30 | 0.46 | 1.77 | | | |
| 11 | 10.5 | 26.4 | 300 | Irganox 1076 (1.82) | 0.26 | 180 | 240 | 1.10 | 0.42 | 1.52 | 15.5 | 9.7 | 14.0 |
| 12 | 10.5 | 24.5 | 300 | — | — | 180 | 240 | 1.32 | 0.50 | 1.82 | | | |
| 13 | 10.5 | 26.4 | 300 | CaSt₂ (5.45) | 0.26 | 180 | 240 | 0.63 | 0.30 | 0.93 | 52.4 | 39.1 | 48.8 |
| 14 | 10.5 | 24.5 | 300 | — | — | 180 | 240 | 1.27 | 0.46 | 1.73 | | | |
| 15 | 10.5 | 26.5 | 300 | CaSt₂ (5.45) + Irganox 1076 (0.91) + Chimassorb 2020 (0.77) | 0.26 | 180 | 240 | 0.69 | 0.34 | 1.03 | 46.0 | 24.5 | 40.4 |

Example 2

This set of examples were performed in a laboratory in a stainless steel vessel. For all experiments 20 milliliters (ml) of dry octene was added to a 50 ml stainless steel vessel inside a nitrogen padded glove box along with the additives described. The vessel was sealed inside the glove box. If hydrogen was used, it was added to pressurize the vessel to 50 psi. The vessel was then removed from the glove box and placed in an oven heated to the desired temperature for 2 hours. After heating, the vessel was opened and the octene sampled in a gas chromatograph. The isomer level in the final material was compared to the isomer level in the original octene sample to determine the % octene isomerized.

Experiment 1—these experiments were conducted in the presence of nickel catalyst. It was found that small amounts of granular nickel would isomerize the octene, most notably in the presence of hydrogen. A variety of different additives were found to decrease the amount of isomerization in the nickel/hydrogen system by levels between 30 and 65%. The results are shown in the Table 2 below.

TABLE 2

| experiment # | nickel added (g) | H₂ added (psi) | additive used | additive amount (g) | isomerization measured (%) | reduction in isomerization (%) |
|---|---|---|---|---|---|---|
| 1* | 0.25 g | 0 | none | 0 | 0.28 | |
| 2* | 0.25 g | 50 | none | 0 | 14.3 | NA |
| 2 (repeat)* | 0.25 g | 50 | none | 0 | 13.3 | NA |
| 3 | 0.25 g | 50 | Dynamar 5920A | 0.25 | 8.1 | 41 |
| 4 | 0.25 g | 50 | trioctylamine | 0.24 | 9.7 | 30 |
| 5 | 0.25 g | 50 | octylamine | 0.23 | 4.9 | 65 |
| 6 | 0.25 g | 50 | Irgafos 168 | 0.25 | 9.3 | 33 |
| 7 | 0.25 g | 50 | Calcium Stearate | 0.25 | 9.3 | 33 |

*= baseline examples

These results show that the inclusion of an additive in either the reactor and/or the heat exchanger reduces the isomerization of 1-octene from 10 to 100, preferably 30 to 70 weight percent when compared with a reaction conducted using the same reactants but without the additive. The addition of these additives has been shown to also reduce isomerization when molecular sieves are present in the reactor.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Furthermore, in describing the arrangement of components in embodiments of the present disclosure, the terms "upstream" and "downstream" are used. These terms have their ordinary meaning. For example, an "upstream" device as used herein refers to a device producing a fluid output stream that is fed to a "downstream" device. Moreover, the "downstream" device is the device receiving the output from the "upstream" device. However, it will be apparent to those skilled in the art that a device may be both "upstream" and "downstream" of the same device in certain configurations, e.g., a system comprising a recycle loop.

The term "and/or" is used to mean both "and" and "or". For example, A and/or B is interpreted to mean A, B or A and B.

What is claimed is:

1. A method for reducing isomerization of α-olefins during the copolymerization of ethylene with an α-olefin comprising:
adding to a reactor a reaction mixture comprising hydrogen, ethylene, an α-olefin, a solvent and a catalyst; where the catalyst does not include a chain shuttling agent that comprises dialkyl zinc; where the reactor is operated at a temperature of 160 to 210° C.;
heating the reactor to a first temperature to react the ethylene with the α-olefin to form a copolymer;
discharging from the reactor a first product stream to a heat exchanger; where the first product stream comprises the copolymer;
adding to the first product stream prior to the heat exchanger a first additive that is operative to reduce isomerization of the α-olefin; where the heat exchanger operates at a higher temperature than the reactor; wherein the first additive is selected from the group consisting of aromatic species having one or more hydroxyl functionalities, fluoropolymers, phosphates, fatty acids, salts of fatty acids, esters of fatty acids, and combinations thereof;
and
discharging from the heat exchanger a second product stream; where a temperature of the second product stream is higher than a temperature of the first product stream.

2. The method of claim 1, further comprising adding a second additive downstream of the reactor and upstream of the heat exchanger, where the second additive is operative to reduce isomerization of the α-olefin.

3. The method of claim 2, further comprising adding a third additive to the second product stream, where the third additive is operative to reduce isomerization of the α-olefin.

4. The method of claim 3, where the first additive is different from the second additive and where the second additive is different from the third additive.

5. The method of claim 3, the second additive and/or the third additive are selected from the group consisting of aromatic species having one or more hydroxyl functionalities, amines, fluoropolymers, phosphates, fatty acids, salts of fatty acids, esters of fatty acids, and combinations thereof.

6. The method of claim 1, where the aromatic species having one or more hydroxyl functionalities have the following structure shown in the formula (1):

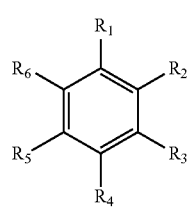

(1)

where one or more of $R_1$ through $R_6$ is a hydroxyl group, with the remainder of $R_1$ through $R_6$ being independently a hydrogen, a substituted or unsubstituted $C_1$-$C_{15}$ alkyl group, a substituted or unsubstituted $C_1$-$C_{15}$ ester group, a substituted or unsubstituted $C_1$-$C_{15}$ cycloalkyl group, or a halogen group.

7. The method of claim 1, where the fluoropolymers include polyvinyl fluoride, polyvinylidene fluoride, polytetrafluoroethylene, polychlorotrifluoroethylene, polyhexafluoropropylene, polyperfluoropropylvinylether, polyperfluoromethylvinylether, or a combination thereof.

8. The method of claim 1, where the fatty acids include saturated or unsaturated fatty acids having 12 to 28 carbon atoms.

9. The method of claim 1, where the salts of fatty acids include sodium, potassium or calcium salts of fatty acids.

10. The method of claim 8, where the fatty acid is stearic acid.

11. The method of claim 9, where the salt of the fatty acid is calcium stearate.

12. The method of claim 1, where an isomerization of the α-olefin is reduced by an amount of 10 to 100 weight percent when compared with a process in which the additive is added only after the heat exchanger.

13. The method of claim 1, where the α-olefin is 1-octene.

14. A method for reducing isomerization of α-olefin during the copolymerization of ethylene with an α-olefin comprising:
adding to a reactor a reaction mixture comprising hydrogen, ethylene, an α-olefin, a first additive, a solvent and a catalyst; where the catalyst does not include a chain shuttling agent that comprises dialkyl zinc; and where the first additive is operative to reduce isomerization of the α-olefin;
heating the reactor to a first temperature to react the ethylene with the α-olefin to form a copolymer; where the reactor is operated at a temperature of 160 to 210° C.;
discharging from the reactor a first product stream to a heat exchanger; where the first product stream comprises the copolymer; and
discharging from the heat exchanger a second product stream; where the heat exchanger operates at a higher temperature than the reactor; where a temperature of the second product stream is higher than a temperature of the first product stream.

15. The method of claim 14, further comprising adding a second additive to the first product stream prior to the heat exchanger; where the second additive is operative to reduce isomerization of the α-olefin.

16. The method of claim 15, further comprising adding a third additive to a product stream at a point downstream of the heat exchanger; where the third additive is operative to reduce isomerization of the α-olefin.

17. The method of claim 16, where the first additive is the same as or different from the second additive and where the first additive and the second additive are the same as or different from the third additive and where the first additive, the second additive and the third additive are selected from the group consisting of aromatic species having one or more hydroxyl functionalities, amines, fluoropolymers, phosphates, fatty acids, salts of fatty acids, esters of fatty acids, and combinations thereof.

18. The method of claim 14, where the α-olefin is 1-octene.

19. A system comprising:
a reactor that is operative to react a reaction mixture comprising hydrogen, ethylene, an α-olefin, a solvent and a catalyst to form a polyethylene copolymer; where the catalyst does not include a chain shuttling agent that comprises dialkyl zinc; where the reactor is operated at a temperature of 160 to 210° C.; and
a heat exchanger that is operative to receive a product stream containing the polyethylene copolymer from the reactor in addition to receiving an additive that is operative to reduce isomerization of the α-olefin, where the heat exchanger operates at a higher temperature than the reactor wherein the additive is selected from the group consisting of aromatic species having one or more hydroxyl functionalities, fluoropolymers, phosphates, fatty acids, salts of fatty acids, esters of fatty acids, and combinations thereof; wherein a product stream emanating from the heat exchanger is at a higher temperature than a temperature of the product stream containing the polyethylene copolymer entering the heat exchanger.

20. The system of claim 19, where the reactor is further operative to receive a portion of the additive.

21. A system comprising:
a reactor that is operative to react a reaction mixture comprising hydrogen, ethylene, an α-olefin, a solvent, an additive and a catalyst to form a polyethylene copolymer; where the catalyst does not include a chain shuttling agent that comprises dialkyl zinc; where the reactor is operated at a temperature of 160 to 210° C.; and where the additive is operative to reduce isomerization of an α-olefin; wherein the additive is selected from the group consisting of aromatic species having one or more hydroxyl functionalities, fluoropolymers, phosphates, fatty acids, salts of fatty acids, esters of fatty acids, and combinations thereof; and
a heat exchanger that is operative to receive a product stream containing the polyethylene copolymer from the reactor, where the heat exchanger operates at a higher temperature than the reactor; wherein a product stream emanating from the heat exchanger is at a higher temperature than a temperature of the product stream containing the polyethylene copolymer entering the heat exchanger.

\* \* \* \* \*